US009763316B2

(12) United States Patent
Nishiuchi et al.

(10) Patent No.: US 9,763,316 B2
(45) Date of Patent: Sep. 12, 2017

(54) CHARGED PARTICLE BEAM RADIATION SYSTEM, SYNCHROTRON, AND BEAM EJECTION METHOD THEREFOR

(71) Applicant: Hitachi, Ltd., Tokyo (JP)

(72) Inventors: Hideaki Nishiuchi, Tokyo (JP); Futaro Ebina, Tokyo (JP); Satoshi Totake, Tokyo (JP); Takuya Nomura, Tokyo (JP); Kunio Moriyama, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/106,876

(22) PCT Filed: Feb. 12, 2015

(86) PCT No.: PCT/JP2015/053721
§ 371 (c)(1),
(2) Date: Jun. 21, 2016

(87) PCT Pub. No.: WO2015/133236
PCT Pub. Date: Sep. 11, 2015

(65) Prior Publication Data
US 2016/0345422 A1   Nov. 24, 2016

(30) Foreign Application Priority Data

Mar. 7, 2014  (JP) ................................. 2014-044524

(51) Int. Cl.
*H05H 15/00* (2006.01)
*H05H 7/10* (2006.01)
(Continued)

(52) U.S. Cl.
CPC ............ *H05H 7/10* (2013.01); *A61N 5/1048* (2013.01); *A61N 5/1077* (2013.01); *H05H 7/02* (2013.01);
(Continued)

(58) Field of Classification Search
CPC ...................... A61N 5/1077; A61N 2005/1087
(Continued)

(56) References Cited

U.S. PATENT DOCUMENTS

| 2,885,552 A * | 5/1959 | Anderson | H05H 13/04 313/62 |
| 6,881,970 B2 * | 4/2005 | Akiyama | A61N 5/10 250/307 |
| 7,875,868 B2 * | 1/2011 | Moriyama | H05H 7/04 250/398 |

FOREIGN PATENT DOCUMENTS

| JP | 2010-227415 A | 10/2010 |
| JP | 2014-079300 A | 5/2014 |

OTHER PUBLICATIONS

Nuclear Instruments and Method in Physics Research A 606 (2009) pp. 325-329.
(Continued)

*Primary Examiner* — Thuy Vinh Tran
(74) *Attorney, Agent, or Firm* — Mattingly & Malur, PC (57) ABSTRACT

When controlling the ejection of a charged particle beam from a synchrotron, a radiofrequency voltage is applied, which serves as the radio-frequency voltage to be applied to an ejection radio-frequency electrode equipping the synchrotron, and which is constituted by a first radio-frequency voltage for increasing an oscillation amplitude in such a way as to exceed a stable limit in order to eject to the exterior of the synchrotron a beam that circles inside the synchrotron, and a second radio-frequency voltage for preferentially ejecting a charged particle beam that circles in the vicinity of the stable limit, with the amplitude value of the second radiofrequency voltage being controlled in such a way that the amplitude value is 0 prior to the beam ejection start, the amplitude value increases gradually from the beam ejection (Continued)

start, and, once a predetermined amplitude value has been reached, this value is maintained.

5 Claims, 4 Drawing Sheets (51) Int. Cl.
    *H05H 13/04*     (2006.01)
    *A61N 5/10*     (2006.01)
    *H05H 7/02*     (2006.01)

(52) U.S. Cl.
    CPC ..... *H05H 13/04* (2013.01); *A61N 2005/1087* (2013.01)

(58) Field of Classification Search
    USPC .......... 315/503, 507; 250/423 R, 424, 492.1, 250/492.3, 493.1
    See application file for complete search history.

(56) References Cited

OTHER PUBLICATIONS

International Search Report of PCT/JP2015/053721 dated Apr. 28, 2015.

\* cited by examiner

| ENERGY | FIRST RADIOFREQUENCY VOLTAGE (Fe) | | | | SECOND RADIOFREQUENCY VOLTAGE (Fm) | |
|---|---|---|---|---|---|---|
| | $f_{ce}$ | $f_{we}$ | $f_{dive}$ | $V_e$ | $f_{cm}$ | $V_m$ |
| E1 | fce_E1 | fwe_E1 | fdive_E1 | Ve_E1 | fcm_E1 | Vm_E1 |
| E2 | fce_E2 | fwe_E2 | fdive_E2 | Ve_E2 | fcm_E2 | Vm_E2 |
| E3 | fce_E3 | fwe_E3 | fdive_E3 | Ve_E3 | fcm_E3 | Vm_E3 |
| : | : | : | : | : | : | : |
| En | fce_En | fwe_En | fdive_En | Ve_En | fcm_En | Vm_En |

CHARGED PARTICLE BEAM RADIATION SYSTEM, SYNCHROTRON, AND BEAM EJECTION METHOD THEREFOR

BACKGROUND ART

As radiation therapy for cancer, there is particle therapy in which a tumor volume of a patient is irradiated with a charged particle beam such as a proton or a heavy ion so as to be treated. A particle therapy system used for such treatment includes a charged particle beam generator, a beam transport system, and an irradiation system. The charged particle beam generator includes a synchrotron or a cyclotron which accelerates a charged particle beam which orbits along a closed orbit to a target energy. An extraction method of a charged particle beam accelerated by a synchrotron has been heavily developed hitherto. PTL 1 and NPL 1 disclose an operation method in which a radiofrequency voltage with a single frequency matching a betatron oscillation frequency of a charged particle beam orbiting around a stability limit is fed in a superimposed manner along with an extraction radiofrequency voltage of the related art so that a particle around the stability limit is preferentially extracted during beam extraction control, and thus the density of charged particle beams around the stability limit is reduced during stoppage of beams in order to prevent the charged particle beams from leaking.

CITATION LIST

Patent Literature

PTL 1: JP-A-2010-227415

Non-Patent Literature

NPL 1: Nuclear Instruments and Method in Physics Research A 606 (2009) P 325 to 329

SUMMARY OF INVENTION

Technical Problem

However, if the radiofrequency voltage obtained by superimposing the radiofrequency voltage with a single frequency on the extraction radiofrequency voltage of the related art is fed to an extraction radiofrequency electrode, leakage of charged particle beams right after stoppage of the beams can be prevented, but an overshoot current is caused when the next beam extraction is started, and thus there is a problem in which it is hard to control an extraction beam current.

An object of the present invention is to provide a charged particle beam irradiation system and a beam extraction method therefor, capable of increasing responsiveness during starting and stopping of extraction of a charged particle beam when controlling extraction of the charged particle beam from a synchrotron and also of suppressing the occurrence of an overshoot current during starting of beam extraction, thereby realizing beam irradiation with high accuracy and also improving a dose rate.

Solution to Problem

In order to achieve the above object, according to the invention, there is provided an extraction control apparatus which extracts a beam orbiting inside a synchrotron to the outside of the synchrotron, the extraction control apparatus including a first radiofrequency voltage output circuit that outputs a first radiofrequency voltage for increasing an oscillation amplitude of the beam so that the beam orbiting inside the synchrotron exceeds a stability limit; a second radiofrequency voltage output circuit that outputs a second radiofrequency voltage for preferentially extracting a charged particle beam orbiting around the stability limit; a combiner that combines the first radiofrequency voltage output from the first radiofrequency voltage output circuit with the second radiofrequency voltage output from the second radiofrequency voltage output circuit and outputs a combined voltage; a radiofrequency amplifier circuit that amplifies a radiofrequency voltage output from the combiner; and a radiofrequency electrode to which the radiofrequency voltage amplified by the radiofrequency amplifier is fed.

An amplitude of the first radiofrequency voltage for increasing an oscillation amplitude of an orbiting beam is controlled depending on a current of the charged particle beam output from the synchrotron, and an amplitude of the second radiofrequency voltage for preferentially extracting a charged particle beam orbiting around the stability limit is set to 0 before starting of beam extraction, and the amplitude of the second radiofrequency voltage is gradually increased at the same time as starting of beam extraction, and is maintained after reaching a predetermined amplitude.

A frequency of the second radiofrequency voltage for preferentially extracting a charged particle beam orbiting around the stability limit is set to a frequency corresponding to a natural oscillation frequency (tune) of the charged particle beam orbiting around the stability limit.

The extraction control apparatus realizing the invention controls feeding (ON) and stoppage (OFF) of the first radiofrequency voltage and the second radiofrequency voltage so that beam extraction (beam ON) and beam stoppage (beam OFF) are performed on the basis of a beam extraction control command (beams ON/OFF command), thereby suppressing leakage of a charged particle beam.

Advantageous Effects of Invention

According to the invention, it is possible to increase response speeds during beam extraction and beam stoppage based on a beam extraction control command for a charged particle beam from a synchrotron, and to suppress the occurrence of an overshoot current during starting of beam extraction, thereby realizing beam irradiation with high accuracy and improving a dose rate.

According to the invention, it is possible to increase response speeds during beam extraction and beam stoppage based on a beam extraction control command only by controlling two radiofrequency voltages, and thus it is possible to easily implement an extraction control system of a synchrotron at low cost.

DESCRIPTION OF EMBODIMENT

Hereinafter, an embodiment of the invention will be described with reference to the drawings.

Example 1

Figure 1:
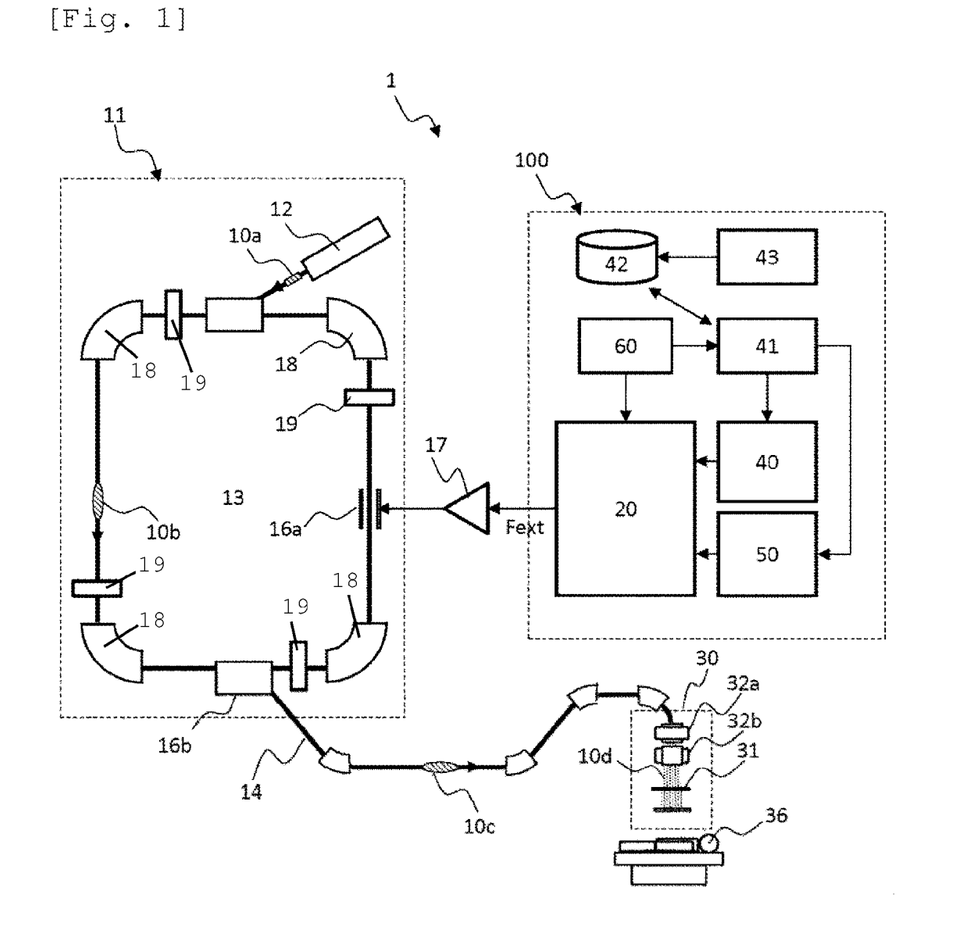
FIG. 1 is a diagram illustrating a configuration of a charged particle beam irradiation system of Example 1 to which the invention is applied.

A charged particle beam irradiation system 1 of the present example includes, as illustrated in FIG. 1, a charged particle beam generator 11, a beam transporter 14, and an irradiation system 30. The beam transporter 14 connects the charged particle beam generator 11 to the irradiation system 30 disposed in a treatment room. The charged particle beam generator 11 includes a synchrotron 13, a pre-accelerator 12, and a synchrotron 13, which accelerate a charged particle beam orbiting along a closed orbit to a desired energy. The pre-accelerator 12 is connected to the synchrotron 13. The pre-accelerator 12 accelerates a charged particle beam 10 to energy which causes the charged particle beam to be injected into the synchrotron 13. A charged particle beam 10a accelerated by the pre-accelerator 12 is injected into the synchrotron 13.

The synchrotron 13 includes a radiofrequency acceleration cavity (hereinafter, referred to as an acceleration cavity), an extraction radiofrequency electrode 16a, and an extraction deflector 16b. The acceleration cavity provides energy to a charged particle beam 10b by feeding a radiofrequency voltage to the charged particle beam 10b orbiting along a closed orbit, and accelerates the charged particle beam until energy of the charged particle beam reaches target energy. The extraction radiofrequency electrode 16a increases a betatron oscillation amplitude of the orbiting charged particle beam, and the extraction deflector 16b extracts the charged particle beam whose oscillation amplitude is increased, from the closed orbit.

When an acceleration radiofrequency voltage is fed to the acceleration cavity, magnetic field intensities of a plurality of bending magnets 18, a plurality of quadrupole magnets 19, and the like, and a frequency of the radiofrequency voltage fed to the acceleration cavity may be increased in accordance with an increase of orbiting energy of the charged particle beam 10b so that a closed orbit of the charged particle beam 10b orbiting inside the synchrotron 13 is constant.

The extraction radiofrequency electrode 16a feeds a radiofrequency magnetic field or a radiofrequency electric field (hereinafter, referred to as a radiofrequency voltage) so as to increase a betatron oscillation amplitude which is the natural oscillation of the orbiting charged particle beam when extracting the charged particle beam reaching the target energy from the synchrotron 13 to a beam transport system. A radiofrequency voltage for increasing the betatron oscillation amplitude with high accuracy may include a band limiting radiofrequency voltage constituted of a plurality of line spectral signals, and an RFKO voltage having undergone frequency modulation in a predetermined frequency range. The charged particle beam whose betatron oscillation amplitude is increased is moved to the outside of a stability limit so as to be extracted from the synchrotron 13 to the beam transporter 14, and is transported to the irradiation system 30.

The irradiation system 30 shapes the charged particle beam guided from the charged particle beam generator 11 in accordance with a depth from a body surface of a patient and a target shape, and feeds the charged particle beam to a target volume of a patient 36 on a treatment bed. As a beam irradiation method in the irradiation system 30, there may be a method in which irradiation and scanning are performed with a beam in accordance with a target shape. A beam scanning method mentioned in the present example indicates a spot scanning irradiation method or a raster scanning irradiation method described below.

In the spot scanning irradiation method, a target volume is divided into regions called spots, and an irradiation dose to be fed to each spot is set according to treatment planning. An irradiation dose for the spot is sequentially measured in a dose monitor 31. If the irradiation dose measured in the dose monitor reaches a predetermined dose, the irradiation with a charged particle beam is stopped. After the irradiation with the charged particle beam is stopped, an excitation amount of a scanning magnet 32 is changed to an excitation amount corresponding to the next spot position, and irradiation with a charged particle beam is performed. Such scanning and irradiation are repeatedly performed, and thus irradiation is performed in a target plane direction. If the irradiation in the target plane direction is completed, a depth direction of the irradiation surface is changed. Irradiation in the target depth direction is controlled by changing a range of the charged particle beam. Specifically, the range of the charged particle beam is changed by changing energy of the charged particle beam supplied to the irradiation system 30.

In the raster scanning method, irradiation and scanning are performed with a charged particle beam along an irradiation path unlike the spot scanning irradiation method. Thus, in the raster scanning irradiation method, a current of the charged particle beam is set to be low in consideration of a temporal structure (spike or ripple) of an extracted beam current, and scanning and irradiation (hereinafter, referred to as repaint) are performed multiple times in the target plane direction, so that predetermined dose uniformity is ensured, and an irradiation dose is completed.

As mentioned above, in the beam scanning method, since irradiation is performed with a charged particle beam matching a target shape, it is not necessary to provide a patient specific device such as a scatterer (SOBP filter), a bolus, or a collimator for forming a uniform absorption dose range (spread-out Bragg peak which is hereinafter referred to as SOBP) matching a target shape unlike a scatterer irradiation method of the related art, and thus it is possible to efficiently irradiate a target volume with a charged particle beam which is supplied from the charged particle beam generator 11 to the irradiation system 30.

The energy of the charged particle beam supplied to the irradiation system 30 may be controlled depending on a frequency of the radiofrequency voltage supplied to the acceleration cavity and a magnetic field intensity of the bending magnet 18. A current of the charged particle beam supplied from the synchrotron 13 to the irradiation system 30 may be controlled depending on an amplitude of the extraction radiofrequency voltage. Charged particle beam irradiation control (beam ON/OFF) for each spot required in the beam scanning method may be realized by controlling feeding (ON) and feeding stoppage (OFF) of the extraction radiofrequency voltage. Particularly, in order to stop (OFF) irradiation with a charged particle beam when an irradiation dose for the spot reaches a predetermined dose, it is necessary to increase accuracy of an irradiation dose by rapidly stopping a charged particle beam extracted from the synchrotron 13. From the viewpoint of treatment efficiency, it is preferable to improve a dose rate by reducing time for irradiating the spot, and, for this, rising of an extracted beam current is preferably fast.

Hereinafter, in the present example, a description will be made of charged particle beam extraction control appropriate for execution of the scanning irradiation method or highly accurate extraction of a charged particle beam. The charged particle beam 10b accelerated to the desired energy establishes a condition (a stability limit 15 of an orbiting beam) in which the orbiting beam 10b can be extracted on the basis of excitation amounts of the quadrupole magnet 19 and a sextupole magnet (not illustrated) according to extraction preparation control. After the extraction preparation control is completed, a radiofrequency voltage (Fext) from an extraction control apparatus 20 is amplified by a radiofrequency amplifier 17 and is then fed to the extraction radiofrequency electrode 16a so that the betatron oscillation amplitude of the beam 10b orbiting inside the synchrotron 13 is increased. The orbiting beam 10b exceeding the stability limit 15 due to the increase of the betatron oscillation amplitude is extracted from the synchrotron 13 to the high energy beam transport 14. Control of extraction of a beam from the synchrotron 13 is performed by controlling beam extraction (feeding of the radiofrequency voltage (Fext)) and beam stoppage (stoppage of the radiofrequency voltage (Fext)) on the basis of the radiofrequency voltage which is fed to the extraction radiofrequency electrode 16a by the extraction control apparatus 20.

A beam 10c extracted from the synchrotron 13 is transported to the irradiation system 30 via the high energy beam transport 14. In the irradiation system 30, a dose intensity of a fed beam 10d is sequentially checked by the dose monitor 31 which measures an irradiation dose of the beam 10d fed to the patient, and the beam 10d is fed in accordance with the target shape by a scanning magnet 32. In order to change a beam range in the target depth direction, the beam 10b is extracted after changing energy of the beam accelerated in the synchrotron 13, and thus a radiation field matching a target shape is formed.

Figure 2:
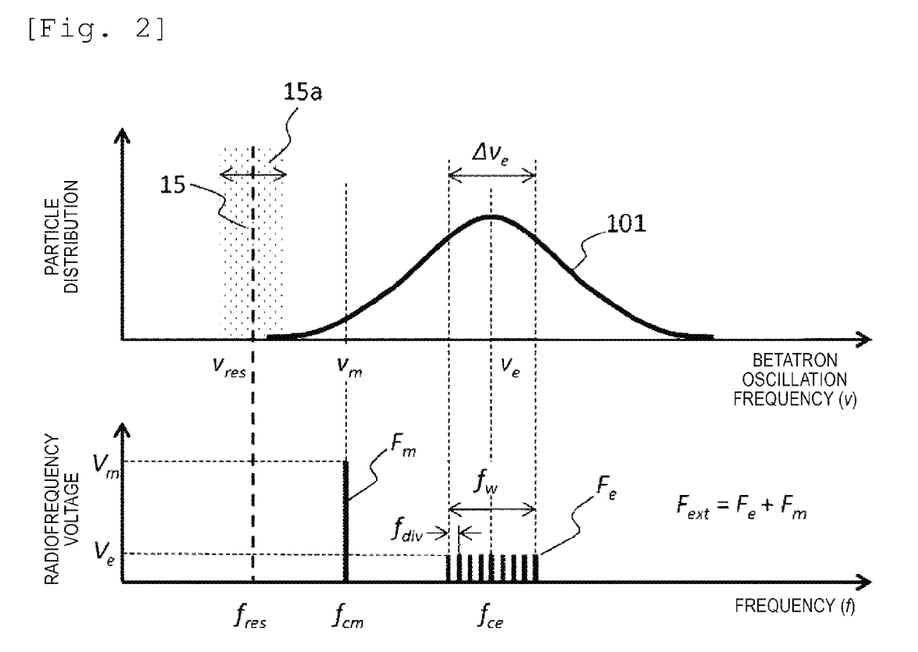
FIG. 2 is a diagram illustrating an feeding band of a radiofrequency voltage fed to an extraction radiofrequency electrode which is a feature of Example 1 to which the invention is applied.

Next, a method of feeding the radiofrequency voltage (Fext) as a feature of the present example will be described through comparison with the methods of the related art with reference to FIGS. 2 and 6. FIG. 2 is a diagram illustrating a feeding band of a radiofrequency voltage fed to the extraction radiofrequency electrode which is a feature of the present example.

As illustrated in FIG. 2, the radiofrequency voltage (Fext) fed to the extraction radiofrequency electrode includes a first radiofrequency voltage for increasing an oscillation amplitude so that the orbiting beam 10b exceeds the stability limit 15, and a second radiofrequency voltage for preferentially extracting a charged particle beam orbiting around the stability limit. In the present example, the first radiofrequency indicates a band limiting radiofrequency voltage constituted of a plurality of line spectral signals, and the second radiofrequency voltage indicates a radiofrequency voltage with a single frequency.

The first radiofrequency voltage for increasing the oscillation amplitude of the orbiting beam 10b up to the stability limit 15 is a band limiting radiofrequency voltage in which a frequency bandwidth relative to a center frequency fce is indicated by fw, and a frequency interval is indicated by fdiv, and is constituted of a plurality of sinusoidal RF voltages. Here, the center frequency fce has a relationship illustrated in Equation 1 with respect to a betatron oscillation frequency (νe) of the orbiting beam. Here, frev is an revolution frequency of the orbiting beam, and n is an integer. Similarly, the frequency bandwidth fw has a relationship shown in Equation 2 with respect to spread (Δνe) of the betatron oscillation frequency of the orbiting beam.

$$fce = \nu e \times n \times frev \quad \text{(Equation 1)}$$

$$fw = \Delta \nu e \times frev \quad \text{(Equation 2)}$$

The intensity Ve of the first radiofrequency voltage has a function of adjusting an amplitude Iext of an extracted beam current, and is thus controlled according to an amount of accumulated beams and a target beam current of the charged particle beam 10b orbiting inside the synchrotron 13.

The second radiofrequency voltage has a function of preferentially extracting a charged particle beam orbiting around the stability limit 15. Thus, a frequency fcm of the second radiofrequency voltage is set to a frequency corresponding to a betatron oscillation frequency νm of a particle distributed around a resonance point νres of the betatron oscillation frequency exhibiting the stability limit. The frequency fcm of the second radiofrequency voltage has a relationship shown in Equation 3 with respect to the betatron oscillation frequency νm of the particle distributed around the stability limit.

$$fcm = \nu e \times n \times frev \quad \text{(Equation 3)}$$

A specific feeding frequency fcm of the second radiofrequency voltage is adjusted by measuring a leaking beam after a beam is stopped, and by surveying a point where an amount of leaking beams is equal to or smaller than a predetermined amount. The intensity Vm of the second radiofrequency voltage is made sufficiently higher than the first radiofrequency voltage in order to reduce the density of the orbiting beam 10b distributed around the stability limit.

Figure 3:
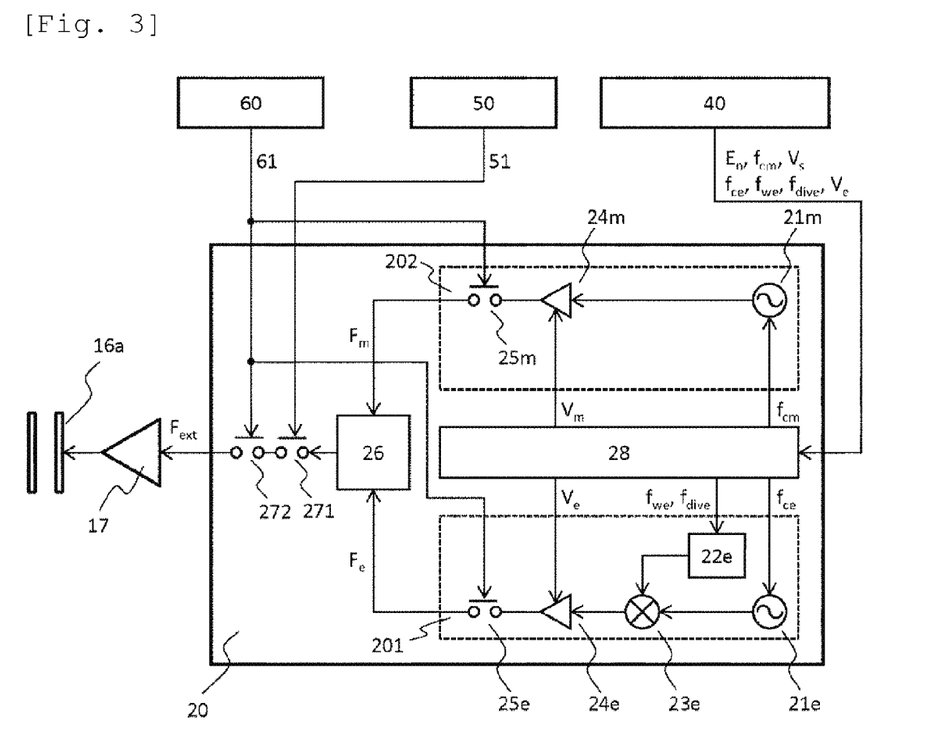
FIG. 3 is a diagram illustrating a configuration of a beam extraction control apparatus for realizing Example 1 to which the invention is applied.

FIG. 3 illustrates a beam extraction control apparatus of the present example. The extraction control apparatus 20 is constituted of a first radiofrequency voltage (Fe) output circuit 201, a second radiofrequency voltage (Fm) output circuit 202, a combiner 26 which combines radiofrequency voltages from the two circuits with each other, radiofrequency switches 271 and 272 which control transmission of a radiofrequency voltage output from the combiner to a radiofrequency amplifier, and a controller 28 which controls a control command value for the radiofrequency voltage output circuits. Extraction beam energy information En and control command values (fce, Ve, fcm, fw, fdiv, and Vm) for the radiofrequency voltages are transmitted from a high-order control system 40 to the controller 28. Control signals are transmitted to radiofrequency switches 25m, 25e, 271 and 272 constituting the extraction control apparatus 20 from a timing system 50 and an interlock system 60. A timing signal 51 indicating a beam extraction control interval is transmitted to the radiofrequency switch 271 of the extraction control apparatus 20 from the timing system 50. After soundness of the control apparatus constituting a particle therapy system 1 is checked, a beam extraction control command 61 is transmitted from the interlock system 60 to the radiofrequency switches 25m, 25e and 272 of the extraction control apparatus 20. In the present example, in order to realize reliable ON/OFF control on an extraction radiofrequency voltage, the three radiofrequency switches 25m, 25e and 272 are redundantly provided, but, in a case where control is desired to be simply performed, only the radiofrequency switch 272 for controlling a radiofrequency voltage transmitted from the combiner 26 may be provided.

Regarding the radiofrequency voltage (Fext) fed to the extraction radiofrequency electrode 16a, the first radiofrequency voltage (Fe) and the second radiofrequency voltage (Fm) are respectively generated by the output circuits 201 and 202, the two generated radiofrequency voltages (Fe and Fm) are combined with each other by the combiner 26 so as to be amplified by the radiofrequency amplifier 17, and then the combined radiofrequency voltage is fed to the extraction radiofrequency electrode 16a.

A description will be made of each of the output circuits 201 (first radiofrequency output circuit) and 202 (second radiofrequency output circuit) of the first radiofrequency voltage (Fe) and the second radiofrequency voltage (Fm).

The output circuit 201 of the first radiofrequency voltage (Fe) will be described. The first radiofrequency voltage output circuit 201 is constituted of an oscillator 21e which outputs the frequency (fce) of the first radiofrequency voltage (Fe), a band limiting radiofrequency generator 22e, a multiplier 23e which multiplies output signals from the oscillator 21e and the band limiting radiofrequency generator 22e, an amplitude modulation circuit 24e, and a radiofrequency switch 25e.

The center frequency (fce) of the first radiofrequency voltage is set in the sinusoidal oscillator 21e by the controller 28, and the band limiting radiofrequency generator 22e outputs a band limiting radiofrequency voltage constituted of a plurality of line spectral signals on the basis of set values of the spectral width (fw) and the spectral interval (fdiv) set by the controller 28.

In the present example, the first radiofrequency voltage (Fe) is generated by using a band limiting voltage constituted of a plurality of line spectra, but may be generated by using a band-pass filter (not illustrated) which outputs an output voltage from a white noise generator (not illustrated) only within the frequency range (fw) of the first radiofrequency voltage (Fe). An output frequency of the sinusoidal oscillator 21e may be swept within the frequency range (fw) of the first radiofrequency voltage (Fe) without using the band limiting radiofrequency generator 22e and the multiplier 23e.

The amplitude (Ve) of the first radiofrequency voltage (Fe) is controlled with respect to a frequency calculation result of the first radiofrequency voltage (Fe) by the amplitude modulation circuit 24e. The first radiofrequency voltage (Fe) having undergone the amplitude modulation control is used to control the radiofrequency switch 25e on the basis of the beam extraction control command 61 output from the interlock system 60. An RF signal is fed during beam extraction, and thus the radiofrequency switch 25e is closed. When the beam is stopped, the RF signal stops being fed, and thus the radiofrequency switch 25e is opened. The first radiofrequency voltage (Fe) which is output via the radiofrequency switch 25e is input to the combiner 26.

Similarly, the second radiofrequency voltage output circuit 202 is constituted of an oscillator 21m which outputs the frequency (fcm) of the second radiofrequency voltage (Fm), an amplitude modulation circuit 24m, and a radiofrequency switch 25m. The oscillator 21m outputs a sinusoidal voltage with the center frequency (fcm) which is set by the controller 28.

The amplitude (Vm) of the second radiofrequency voltage (Fm) set by the controller 28 is controlled with respect to the second radiofrequency voltage (Fm) by the amplitude modulation circuit 24m. The second radiofrequency voltage (Fm) having undergone the amplitude control is used to control the radiofrequency switch 25m on the basis of the beam extraction control command 61 output from the interlock system 60. An RF signal is fed during beam extraction, and thus the radiofrequency switch 25m is closed. When the beam is stopped, the RF signal stops being fed, and thus the radiofrequency switch 25m is opened. The second radiofrequency voltage (Fm) which is output via the radiofrequency switch 25m is input to the combiner 26.

The combiner 26 combines the two radiofrequency voltages (Fm and Fe) with each other. The combined radiofrequency voltage (third radiofrequency voltage) is output to the radiofrequency amplifier 17 via the two radiofrequency switches 271 and 272.

Figure 4:
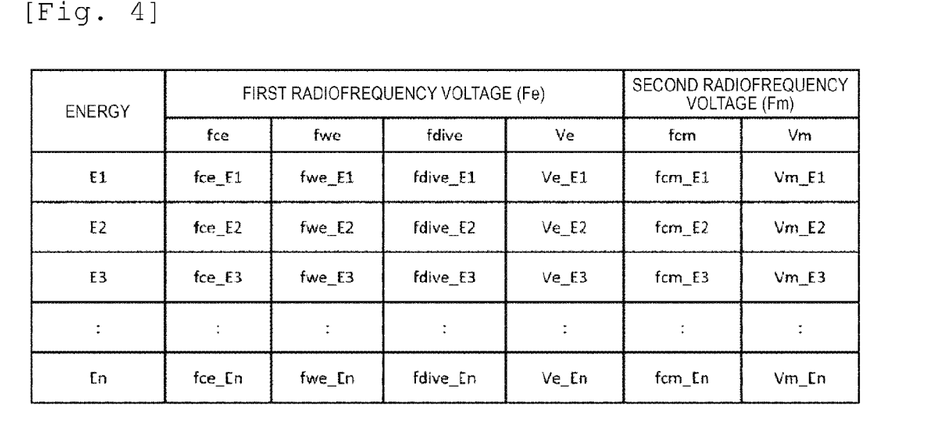
FIG. 4 is a diagram illustrating a relationship between a control command value of the extraction control apparatus for realizing Example 1 to which the invention is applied, and extraction beam energy.

With reference to FIGS. 3 and 4, a description will be made of a method of managing control set values in each control circuit from the controller 28 of the extraction control apparatus 20. Control set values of the first radiofrequency voltage (Fe) and the second radiofrequency voltage (Fm) include, as illustrated in FIG. 4, the central frequencies (fcs and fce) in the sinusoidal oscillators 21, and the spectral width (fw), the spectral interval (fdiv), and the amplitudes (Vs and Ve) of the band limiting signal, which are stored in advance in a memory (not illustrated) of the controller 28 in correlation with the extraction beam energy information (En). The extraction beam energy information (En) of the synchrotron 13 is transmitted from the high-order control system 40 to the extraction control apparatus 20 on the basis of treatment planning information. The controller 28 reads the control set values stored in the memory, and outputs the control set values to each control circuit, on the basis of the extraction beam energy information (En) transmitted from the high-order control system 40.

A description will be made of control of the intensity of the radiofrequency voltage (Fext) fed to the extraction radiofrequency electrode. In the method of the related art, when a beam is extracted (beam ON), as illustrated in FIG. 6, an extraction radiofrequency voltage (FIG. 6(b)) which is the first radiofrequency voltage and a second radiofrequency voltage (FIG. 6(c)) which is the second radiofrequency voltage are simultaneously fed during beam extraction (beam ON) on the basis of a beam extraction control command (FIG. 6(a)). When the beam is stopped (beam OFF), the extraction radiofrequency voltage (FIG. 6(b)) which is the first radiofrequency voltage and the second radiofrequency voltage (FIG. 6(c)) which is the second radiofrequency voltage simultaneously stop being fed. Therefore, the output circuit 202 and the output circuit 201 may also be recognized as a synchronously functioning configuration.

Figure 6:
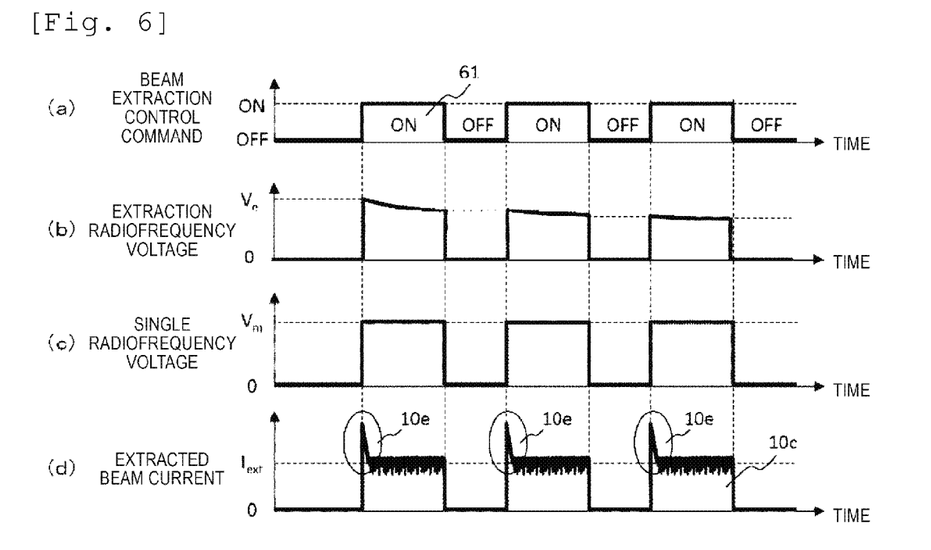
FIG. 6 is a diagram illustrating a timing chart during beam extraction control of the related art.

Here, in the method of the related art, the second radiofrequency voltage (FIG. 6(c)) is fed in a stepwise manner in response to the beam extraction (beam ON) command. Thus, since the orbiting beam 10b distributed around the stability limit 15 illustrated in FIG. 2 is extracted at the same time as starting of beam extraction, this causes an overshoot 10e in an extracted beam current waveform (FIG. 6(d)), and thus there is a problem in that it is hard to control an extracted beam current.

Figure 5:
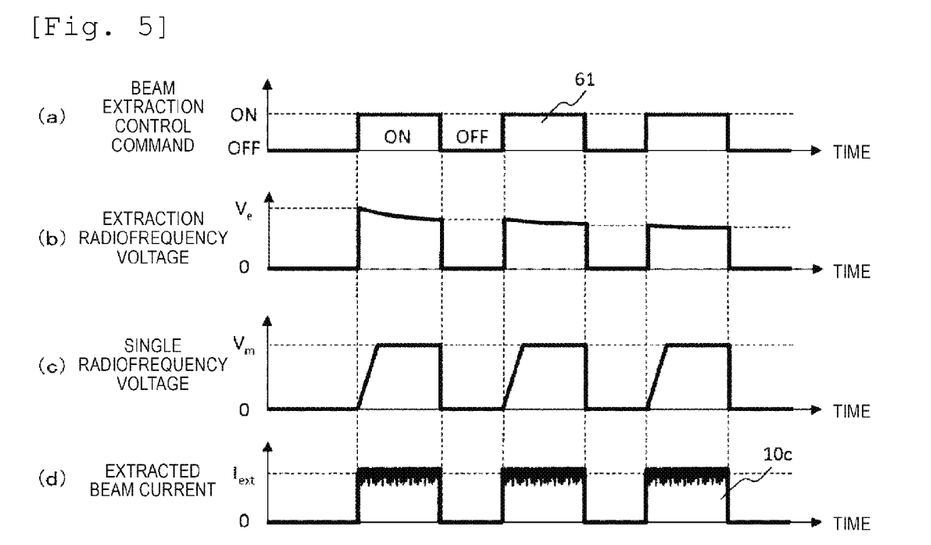
FIG. 5 is a diagram illustrating a timing chart during beam extraction control in Example 1 to which the invention is applied.

On the other hand, as illustrated in FIG. 5, the charged particle beam irradiation system of the present example feeds an extraction radiofrequency voltage (FIG. 3(b)) which is the first radiofrequency voltage and a second radiofrequency voltage (FIG. 5(c)) which is the second radiofrequency voltage during beam extraction (beam ON)

on the basis of a beam extraction control command (FIG. 5(a)). However, at this time, the second radiofrequency voltage (FIG. 5(c)) which is the second radiofrequency voltage is gradually increased from 0, and the second radiofrequency voltage is fed at a constant value after reaching a predetermined value. As mentioned above, by controlling the second radiofrequency voltage (FIG. 5(c)) which is the second radiofrequency voltage, the orbiting beams 10b distributed around the stability limit 15 are not simultaneously extracted, that is, it is possible to suppress the occurrence of the overshoot 10e in an extracted beam current 10c.

PTL 1 discloses the content that feeding of an acceleration radiofrequency voltage and an extraction radiofrequency voltage is controlled on the basis of a beam extraction command, and the extraction radiofrequency voltage is gradually increased from 0 during beam extraction (beam ON), and is fed at a constant value if reaching a predetermined irradiation dose. If such feeding control of the extraction radiofrequency voltage is performed, an overshoot of an extracted beam current can be suppressed at the time of starting of beam extraction, but rising of the extracted beam current is smoothened in order to suppress the overshoot. Therefore, there may be a problem in that time for irradiating a corresponding spot is taken, and a dose rate is reduced.

In contrast, in the present example, of the first radiofrequency voltage for increasing the oscillation amplitude so that the orbiting beam 10b exceeds the stability limit 15, and the second radiofrequency voltage for preferentially extracting a charged particle beam orbiting around the stability limit, only the amplitude of the second radiofrequency voltage for preferentially extracting the charged particle beam orbiting around the stability limit is gradually increased from 0, and the second radiofrequency voltage is fed at a constant value after reaching a predetermined value. Thus, since the orbiting beam 10b is extracted, and the amplitude of the first radiofrequency voltage fed for controlling an extracted beam current is controlled so as to realize a predetermined extracted beam current, rising of the extracted beam current is not smoothened unlike PTL 1. Therefore, irradiation time for a corresponding spot is not long, and a reduction in a dose rate can also be suppressed.

As described above, a voltage obtained by superimposing the first radiofrequency voltage for increasing the oscillation amplitude so that a charged particle beam orbiting inside the synchrotron 13 exceeds the stability limit and the second radiofrequency voltage for preferentially extracting a charged particle beam orbiting around the stability limit on each other is fed to the extraction radiofrequency electrode 16a, and the amplitudes of the first radiofrequency voltage and the second radiofrequency voltage are separately controlled, so that responsiveness during starting and stoppage of extraction of the charged particle beam can be increased when controlling extraction of the charged particle beam from the synchrotron 13, and the occurrence of an overshoot current during starting of beam extraction can also be suppressed. Consequently, it is possible to provide a charged particle beam irradiation system and an extraction method therefor capable of realizing beam irradiation with high accuracy and improving a dose rate.

Specifically, the first radiofrequency voltage is generated by using a band limiting radiofrequency voltage constituted of a plurality of frequency components, a frequency range of the first radiofrequency voltage is set so that an orbiting beam exceeds the stability limit, and the intensity of the first radiofrequency voltage is controlled depending on an extracted beam current to be obtained. A frequency of the second radiofrequency voltage is set between the stability limit and the center frequency of the first radiofrequency voltage, and the intensity of the second radiofrequency voltage is controlled to be increased at the same time as starting of beam extraction and to be constant after reaching a predetermined voltage amplitude. Consequently, it is possible to increase beam control responsiveness, that is, response speeds during beam extraction and beam stoppage based on a beam extraction control command.

The invention is not limited to the configuration described in the embodiment, and a configuration thereof can be changed as appropriate within the scope without departing from the spirit of the invention disclosed in the claims. The above-described embodiment has been described in detail for better understanding of the invention, and is not limited to including all the described configurations.

REFERENCE SIGNS LIST

1 CHARGED PARTICLE BEAM IRRADIATION SYSTEM
100 CONTROL SYSTEM (CONTROL APPARATUS)
10a, 10b, 10c, AND 10d BEAM
10e OVERSHOOT OF EXTRACTED BEAM CURRENT
101 ORBITING BEAM DISTRIBUTION
11 CHARGED PARTICLE BEAM GENERATOR
12 PREACCELERATOR
13 SYNCHROTRON
14 BEAM TRANSPORTER
15 STABILITY LIMIT
16a EXTRACTION RADIOFREQUENCY ELECTRODE
16b EXTRACTION DEFLECTOR
17 RADIOFREQUENCY AMPLIFIER
18 BENDING MAGNET
19 QUADRUPOLE MAGNET
20 EXTRACTION CONTROL APPARATUS
201 FIRST RADIOFREQUENCY VOLTAGE OUTPUT CIRCUIT (FIRST RADIOFREQUENCY VOLTAGE GENERATION CIRCUIT)
202 SECOND RADIOFREQUENCY VOLTAGE OUTPUT CIRCUIT (SECOND RADIOFREQUENCY VOLTAGE GENERATION CIRCUIT)
21m AND 21e SINUSOIDAL OSCILLATOR
22e BAND LIMITING RADIOFREQUENCY GENERATOR
23e MULTIPLIER
231 SWITCH
24m AND 24e AMPLITUDE MODULATOR
25m AND 25e RADIOFREQUENCY SWITCH
26 AND 261 COMBINER
271 AND 272 RADIOFREQUENCY SWITCH
28 CONTROLLER
30 IRRADIATION SYSTEM
31 DOSE MONITOR
32 SCANNING MAGNET
36 PATIENT
40 ACCELERATOR CONTROL APPARATUS
41 COLLECTIVE CONTROL APPARATUS
42 STORAGE APPARATUS
43 TREATMENT PLANNING SYSTEM
431 TREATMENT PLANNING INFORMATION
50 TIMING SYSTEM

51 TIMING SIGNAL
60 INTERLOCK SYSTEM
61 BEAM EXTRACTION CONTROL COMMAND

The invention claimed is:

1. A charged particle beam irradiation system comprising:
a synchrotron that accelerates and extracts a charged particle beam;
an irradiation system that performs irradiation with the charged particle beam extracted from the synchrotron; and
an extraction control apparatus that extracts a beam orbiting inside the synchrotron to the outside of the synchrotron,
wherein the extraction control apparatus includes:
a first radiofrequency (RF) voltage output circuit that outputs a first RF voltage for increasing an oscillation amplitude of the beam so that the beam orbiting inside the synchrotron exceeds a stability limit;
a second RF voltage output circuit that outputs a second RF voltage for preferentially extracting a charged particle beam orbiting around the stability limit;
a combiner that combines the first RF voltage output from the first RF voltage output circuit with the second RF voltage output from the second RF voltage output circuit, and outputs a combined voltage;
a RF amplifier circuit that amplifies a RF voltage output from the combiner; and
a RF electrode to which the RF voltage amplified by the RF amplifier circuit is fed,
wherein an amplitude of the first RF voltage is controlled depending on a current of the charged particle beam output from the synchrotron, and
wherein an amplitude of the second RF voltage is set to 0 before starting beam extraction, the amplitude of the second RF voltage is gradually increased at the same time as the starting of beam extraction, and the amplitude of the second RF voltage is maintained after reaching a predetermined amplitude.

2. The charged particle beam irradiation system according to claim 1,
wherein a frequency of the second radiofrequency voltage for preferentially extracting the charged particle beam orbiting around a stability limit is set to a frequency corresponding to a betatron oscillation frequency of the charged particle beam orbiting around the stability limit.

3. The charged particle beam irradiation system according to claim 1,
wherein the extraction control apparatus controls feeding and stoppage of the first radiofrequency voltage and the second radiofrequency voltage so that the beam extraction and beam stoppage are performed on the basis of a beam extraction control command.

4. A synchrotron which accelerates and extracts a charged particle beam, the synchrotron comprising:
an extraction control apparatus including:
a first RF voltage output circuit that outputs a first RF voltage for increasing an oscillation amplitude of a beam orbiting inside the synchrotron so that the beam exceeds a stability limit in order to extract the beam to the outside of the synchrotron;
a second RF voltage output circuit that outputs a second RF voltage for preferentially extracting a charged particle beam orbiting around the stability limit;
a combiner that combines the first RF voltage output from the first RF voltage output circuit with the second RF voltage output from the second RF voltage output circuit, and outputs a combined voltage;
a RF amplifier circuit that amplifies a RF voltage output from the combiner; and
a RF electrode that feeds the RF voltage amplified by the RF amplifier circuit,
wherein an amplitude of the first RF voltage is controlled depending on a current of the charged particle beam output from the synchrotron, and
wherein an amplitude of the second RF voltage is set to 0 before starting beam extraction, the amplitude of the second RF voltage is gradually increased at the same time as the starting of beam extraction, and the amplitude of the second RF voltage is maintained after reaching a predetermined amplitude.

5. A beam extraction method for a charged particle beam irradiation system including a synchrotron that accelerates and extracts a charged particle beam, and an irradiation system that performs irradiation with the charged particle beam extracted from the synchrotron, the method comprising:
a step of feeding, to a RF electrode, a first RF voltage for increasing an oscillation amplitude of a beam orbiting inside the synchrotron so that the beam exceeds a stability limit in order to extract the beam to the outside of the synchrotron, a second RF voltage for preferentially extracting a charged particle beam orbiting around the stability limit, and a RF voltage obtained by combining the first RF voltage with the second RF voltage and by amplifying a RF voltage output from the combiner with an amplifier,
wherein an amplitude of the first RF voltage for increasing an oscillation amplitude of an orbiting beam is controlled depending on a current of the charged particle beam output from the synchrotron, and
wherein an amplitude of the second RF voltage for preferentially extracting the charged particle beam orbiting around the stability limit is set to 0 before starting beam extraction, the amplitude of the second RF voltage is gradually increased at the same time as the starting of beam extraction, and the amplitude of the second RF voltage is maintained after reaching a predetermined amplitude.

* * * * *